(12) United States Patent
Müssig

(10) Patent No.: US 6,428,218 B1
(45) Date of Patent: Aug. 6, 2002

(54) METHOD AND DEVICE FOR SPLICING OPTICAL CONDUCTORS

(75) Inventor: Dirk Müssig, München (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/647,163

(22) PCT Filed: Mar. 23, 1999

(86) PCT No.: PCT/DE99/00850

§ 371 (c)(1),
(2), (4) Date: Sep. 26, 2000

(87) PCT Pub. No.: WO99/50698

PCT Pub. Date: Oct. 7, 1999

(30) Foreign Application Priority Data

Mar. 27, 1998 (DE) .......................................... 198 13 755

(51) Int. Cl.⁷ .............................................. G02B 6/255
(52) U.S. Cl. .............................. 385/96; 385/95; 385/97; 385/98; 219/121.13; 219/121.14
(58) Field of Search .................. 385/95, 96, 97, 385/98; 219/121.13, 121.14

(56) References Cited

U.S. PATENT DOCUMENTS

| 4,049,414 | A | | 9/1977 | Smith | |
|---|---|---|---|---|---|
| 4,506,947 | A | | 3/1985 | Tatekura et al. | |
| 4,561,719 | A | * | 12/1985 | Quan | 350/96.21 |
| 5,228,102 | A | * | 7/1993 | Sato et al. | 385/95 |
| 5,414,788 | A | * | 5/1995 | Kammlott et al. | 385/96 |
| 5,909,527 | A | * | 6/1999 | Zheng | 385/96 |
| 6,062,743 | A | * | 5/2000 | Zheng et al. | 385/95 |
| 6,186,675 | B1 | * | 2/2001 | Ruegenberg | 385/96 |
| 6,294,760 | B1 | * | 9/2001 | Inoue et al. | 219/383 |
| 6,336,750 | B1 | * | 1/2002 | Clark et al. | 385/96 |

FOREIGN PATENT DOCUMENTS

| DE | 196 17 388 | 5/1997 |
|---|---|---|
| EP | 0 576 266 | 12/1993 |
| EP | 0 864 889 | 2/1998 |
| EP | 0 864 890 | 2/1998 |

OTHER PUBLICATIONS

Database WPI, Section PQ, Week 9409, Derwent Publications Ltd., London, GB; Class P81, AN 94–073392 XP002114156 & SE 9 201 817 A (Telefonaktiebolaget Ericsson LM) Dec. 13, 1993.

Wenxin Zheng, "Real Time Control of Arc Fusion of Optical Fiber Splicing", *Journal of Lightwave Technology*, vol. 11, No. 4, Apr. 1993, pp. 548–553.

Abstract of Japanese Published Application 02028605, *Patent Abstracts of Japan*, vol. 014, No. 179 (p–1034), Apr. 10, 1990.

* cited by examiner

*Primary Examiner*—John D. Lee
*Assistant Examiner*—Jennifer Doan
(74) *Attorney, Agent, or Firm*—Schiff Hardin & Waite

(57) ABSTRACT

In a process of splicing optical fibers, a temperature distribution during the splicing of the waveguides at a constant discharge current will depend on ambient parameters, which include temperature, air pressure and air humidity, and these parameters also influence the quality of the splice being produced. The discharge current is regulated by measuring the actual intensity distribution of the thermionic emissions of the waveguide during the splicing operation and by comparing this intensity distribution with a stored reference intensity distribution. The device includes a sensor which is used for measuring the intensity distribution and for adjusting the ends of the waveguides relative to each other.

14 Claims, 1 Drawing Sheet

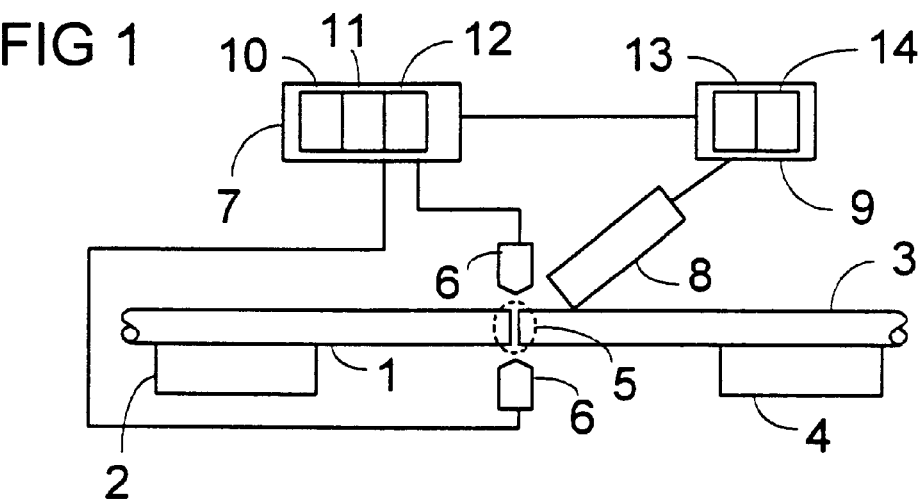
FIG 1
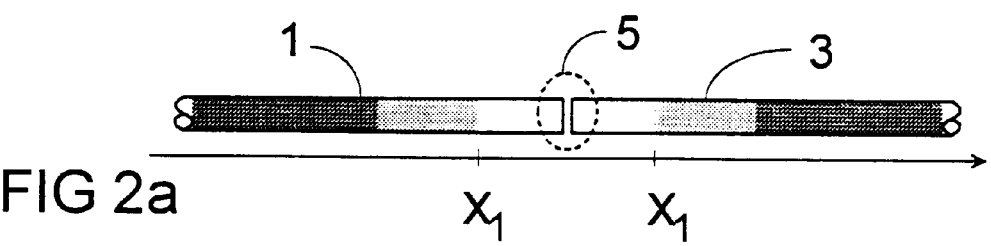
FIG 2a
FIG 2b

METHOD AND DEVICE FOR SPLICING OPTICAL CONDUCTORS

The invention relates to a method for splicing optical conductors by using an arc discharge between two electrodes and controlling the arc discharge by controlling the discharge current and to a splicing device which has two electrodes, holding devices for positioning the conductors between the electrodes, a current source for striking an arc discharge between the electrodes and a set point generator for providing a preset discharge current for the source.

Two methods are known for connecting the optical conductors (glass or polymer fibers) which are being increasingly used in optical telecommunications engineering: on the one hand, bonding ends of the optical conductors in preassembled and standardized connectors and, on the other hand, splicing optical conductors with prepared end faces to form a single optical conductor. When splicing the optical conductors in splicing devices, two optical conductors with prepared end faces are fastened on two holding devices which can then be moved with the aid of adjusting devices so that the end faces are well adjusted relative to one another. After the adjustment, the two ends are then, in general, thermally welded. The thermal welding is performed in this case using an arc discharge between two electrodes.

U.S. Pat. No. 4,506,947 discloses a method in which a video camera is used to adjust two glass fibers relative to one another in a controlled fashion by illuminating the splice point with ultraviolet light so that the core of the glass fibers, which is doped with germanium, emits light in the visible wavelength region. The light is displayed on a monitor via the video camera and a downstream image evaluation unit. The operator of the device can therefore adjust the cores of the two glass fibers relative to one another via the monitoring device and the adjusting device. The quality of the splicing operation is not observed.

The quality of a splice which is intended to achieve optical losses as small as possible during the transmission of light from one optical conductor into the other, depends essentially on the parameters set in the splicing device. The discharge current used to weld the optical conductors is also one of these parameters. In the case of optimum adjustment and constant ambient conditions (air pressure, air humidity, temperature), heating which remains good is achieved with the aid of a constant discharge current. In the case of altered ambient conditions and used or soiled electrodes, there is a change in the heating of the optical conductors even given a constant discharge current, and thus a change in the quality of splicing.

In the field of material processing of work pieces using lasers, DE 196 17 388 discloses a method which uses video sensors to evaluate the temperature distribution in a plasma initiated by a laser. The plasma corresponds to the arc discharge during splicing, but the method can provide no information either on the temperature distribution in the optical conductor itself, or thus on the quality of the splice.

SUMMARY OF THE INVENTION

It is therefore the object of the invention to automate the control of the temperature for a splicing operation independently of ambient parameters.

The object is achieved by means of a method and a splicing device of the type mentioned at the beginning by using a sensor to measure the actual intensity distribution occurring during splicing, storing a reference intensity distribution in a storage device, comparing the measured intensity distribution with the reference intensity distribution and correcting the discharge current in a controller in response to any deviations therebetween.

For this purpose, the actual intensity distribution occurring in the case of optical conductors which emit thermionically upon the application of a preset discharge current is measured and compared with a stored reference intensity distribution. Intensity distribution is understood below as a spatially resolved (if appropriate, also wavelength-resolved) image of the ends of the optical conductors. In the case of a deviation, the discharge current is then varied such that the actual intensity distribution attained at least approaches the stored reference intensity distribution. This results in automated control of the discharge current which is independent of ambient parameters, and so splicing operations lead to identical temperature distributions in the optical conductors, and thus to a quality of the splices which remains good.

The newly determined, adapted discharge current is advantageously stored as a preset discharge current for future splicing operations.

When color cameras are used, the reference intensity distribution can be stored in a wavelength-resolved fashion and compared with wavelength-resolved actual intensity distributions during the splicing operations in order to arrive at a more accurate statement on the temperature distribution in the optical conductors.

When black and white cameras are used gray-scale values are advantageously assigned to the intensity distributions.

The gray-scale values determined in the process are averaged over the area of the two optical conductors, and only this mean gray-scale value of the actual intensity distribution is compared with a mean reference gray-scale value. The quantity of data to be stored is advantageously reduced by this process.

In a preferred embodiment, the gray-scale values of a row of the optical sensor are evaluated in the direction of the axes of the two optical conductors in a spatially resolved fashion. The actual position of a prescribed gray-scale value which occurs is compared with a stored reference position of the prescribed gray-scale value, and in the case of a deviation the discharge current is corrected such that the actual position approaches the reference position. The quantity of data to be stored is also reduced by this embodiment.

A temporal actual sequence of intensity distributions is advantageously stored and compared with a stored reference sequence in order to arrive at a yet more accurate statement on the temperature distribution during the splicing operation.

A particularly reproducible method is achieved by virtue of the fact that the temporal sequence is triggered by the application of the discharge current.

In the case of the splicing device, a memory is provided for storing the reference intensity distribution in order thereby to compare in a comparator the actual intensity distribution measured with the aid of a sensor. A controller serves the purpose of controlling the discharge current as a function of the comparison made.

For the purpose of a simple construction in conjunction with reduced costs, the sensor is designed such that it can also be used to adjust the ends of the optical conductors.

The invention is explained in more detail in exemplary embodiments with the aid of the figures of the drawins.

BRIEF DESCRIPTION OF THE DRAWINGS

FIG. 1 shows a schematic of the inventive splicing device for splicing optical conductors, FIG. 2a shows a schematic of the intensity distribution over the longitudinal axis of the two optical conductors in the case of a first temperature distribution, and FIG. 2b shows a schematic of the intensity distribution over the longitudinal axis of the two optical conductors in the case of a second temperature distribution.

DESCRIPTION OF THE PREFFERRED EMBODIMENTS

In accordance with FIG. 1, for splicing purposes the end of a first optical conductor 1 is fastened on a first holding device 2. A second optical conductor 3 is fastened on a second holding device 4. The holding devices 2, 4 also serve as adjusting devices with the aid of which the two ends of the optical conductors 1, 3 can be adjusted to a minimum offset relative to one another so as to produce an additional optical loss which is as small as possible at the transition point (splice point) from the first optical conductor 1 to the second optical conductor 3. The two ends of the optical conductors 1, 3 are welded to one another by striking an arc 5 between two electrodes 6. In this case, a prescribed discharge current is applied to the two electrodes 6 by a control device 7 which comprises a current source 10 and an assigned setpoint generator 11.

According to the invention, the region of the arc 5 with the ends of the optical conductors 1, 3 is picked up by a sensor 8, for example a video camera, and evaluated in a downstream image evaluation unit 9. The image evaluation unit 9 here comprises a storage device 13 for storing a reference intensity distribution and a comparator 14 for comparing the actual intensity distribution with the reference intensity distribution. A controller 12 is driven as a function of the comparison and, for its part, controls the discharge current via the setpoint generator 11 assigned to the current source 10 in such a way that the actual intensity distribution at least approaches the reference intensity distribution. Of course, the greatest possible approach is targeted, in order to obtain a reproducible quality for the splice.

The sensor 8 with the downstream image evaluation unit 9 can also advantageously be used to adjust the optical conductors, thus resulting in a design of the splicing device which is simplified by comparison with a device with two sensors.

In order to be able to measure the change in intensity, it is necessary to dispense with an automatic gain control of the sensor 8 when applying the method. If the offset of the two optical conductors relative to one another is measured using light injected into the optical conductors, this injected light must be excluded during the splicing operation in order for it not to influence the intensity distribution to be measured.

The reference intensity distribution has been determined, for example, during a "training phase" in which various intensity distributions attained with the aid of various discharge currents are stored, the quality of the splices resulting therefrom is investigated, and the intensity distribution for the splice with the smallest losses is subsequently stored as a reference intensity distribution, and the associated discharge current is stored as a preset discharge current.

Upon application of the preset discharge current, the ends of the optical conductors begin to emit thermonic radiation in the region of the arc 5 and thus to emit light in the visible region of the spectrum. The temperature distribution in the optical conductors will have a maximum in the region of the arc 5 and decrease in the optical conductors 1, 3 with an increase of the distance from the arc 5. The brightness of the radiated thermonic emission will likewise decrease with an increase of the distance from the arc 5.

In the case when the ambient parameters have changed, an actual intensity distribution which deviates from the reference intensity distribution will result for the preset discharge current. The discharge current is varied with the aid of the controller 12 of the control device 7 until the actual intensity distribution at least approaches the reference intensity distribution. In the case of the same intensity distribution, the same temperature distributions is then obtained with the result that a splice with the previously defined optimum minimum losses is attained.

In the case of the use of a color camera, the intensity distributions can be stored in a wavelength-resolved fashion, and this permits a particularly accurate control of the discharge current.

Two methods which manage with a black and white camera are particularly economical with reference to the quantity of data to be stored. Gray-scale values are assigned to the intensity distributions in the black and white camera which acts as the sensor 8.

In the first method, the gray-scale values are averaged in this case over the entire window of the black and white camera, and only the mean gray-scale value of the reference intensity distribution is stored in the storage device 13 of the image evaluation unit 9. Given a higher temperature than envisaged, a higher mean gray-scale value of the actual intensity distribution is measured, and thereby the discharge current is appropriately corrected.

A second method with gray-scale values is illustrated in FIGS. 2a and 2b. In this case, a reference position x1 for a prescribed gray-scale value, which is represented here by the transition of white to light gray, is stored as the reference intensity distribution. If, during further splicing operations, the temperature in the example changes to higher temperatures, the position with the prescribed gray-scale value will now occur at an actual position x2 according to FIG. 2b. The original temperature distribution is achieved in this case by controlling the discharge current and thereupon displacing the actual position x2 in the direction of the reference position x1. It is also possible to pick up and store temporal sequences of the intensity distributions and then compare them with one another during the splicing operations. The temporal sequence of the recordings is triggered in this case by switching on the discharge current.

The result of this is an automated control, which is independent of ambient parameters, of a uniform temperature distribution during splicing of the optical conductors.

I claim:

1. A method for splicing optical conductors, said method comprising creating an arc discharge between two electrodes, which discharge is controlled by a discharge current, using a preset discharge current for striking the arc between said electrodes, measuring a spatially resolved actual intensity distribution of the thermionic emissions occurring during the process at the optical conductors, comparing a spatially resolved reference intensity distribution with the measured distribution to determine a deviation therebetween, correcting the discharge current if a deviation occurs to cause the actual intensity distribution to approach the reference intensity distribution, the improvements comprising assigning a gray-scale value to the actual intensity distribution and the reference intensity distribution, evaluating the gray-scale values along the direction of the axes of the two optical conductors, comparing a reference position in the direction of the two optical conductors for the prescribed gray-scale value with the actual position of the gray-scale value of the actual intensity distribution and when a deviation occurs, controlling the discharge current so that the actual position approaches the reference position.

2. A method according to claim 1, wherein the corrected discharge current is stored as a preset discharge current for following splicing operations.

3. A method according to claim 2, wherein the actual intensity distribution and the reference intensity distribution are stored and compared in a wavelength-resolved fashion.

4. A method according to claim 3, which includes storing a temporal actual sequence of the intensity distribution of the images of the ends during switching on the discharge current, comparing temporal actual sequence with a stored reference sequence of the intensity distribution to determine any deviation therebetween, and controlling the discharge current when a deviation occurs so that the actual sequence at least approaches the reference sequence.

5. A method according to claim 4, which includes applying a discharge current to trigger the temporal actual sequence and the reference sequence.

6. A method according to claim 1, which includes storing the actual intensity distribution and the reference intensity distribution in a wavelength-resolved fashion.

7. A method according to claim 6, which includes storing a temporal actual sequence of the intensity distribution of the images of the ends, comparing the stored reference sequence of the intensity distribution with the temporal actual sequence on switching on of the discharge current to determine a deviation therebetween, and controlling the discharge current when a deviation occurs, so that the actual sequence at least approaches the reference sequence.

8. A method according to claim 7, wherein the temporal actual sequence and reference sequence are triggered by applying the discharge current.

9. A method according to claim 1, which includes storing a temporal actual sequence of the intensity distribution of the images of the ends on switching on of the discharge current and comparing the temporal actual sequence with a stored reference sequence of the intensity distribution to determine a deviation, if a deviation occurs, controlling the discharge current so that the actual sequence at least approaches the reference sequence.

10. A method according to claim 9, wherein the temporal actual sequence and the reference sequence are triggered by applying the discharge current.

11. A method for splicing two optical conductors using an arc discharge between two electrodes, which is controlled by a discharge current, initiating the arc discharge with a preset discharge current, measuring a spatially resolved actual intensity distribution of the thermionic emission occurring in the process along the direction of the axes of the two optical conductors, comparing a spatially resolved reference intensity distribution with the actual intensity distribution to determine a deviation, correcting the discharge current if a deviation appears, so that the actual intensity distribution approaches the reference distribution, and storing a corrected discharge current as a preset discharge current for a following splicing operation.

12. A method for splicing optical conductors according to claim 11, which includes averaging a gray-scale value over the image of the two optical conductors to determine a mean gray-scale value for the reference intensity distribution and a mean gray-scale value for the actual intensity distribution, storing the mean gray-scale value of the reference intensity distribution, comparing the mean gray-scale value of the actual intensity distribution to the mean gray-scale value of the reference intensity distribution to determine a deviation, if a deviation occurs, controlling the discharge current so that the mean gray-scale value of the actual intensity distribution approaches the mean gray-scale value of the reference intensity distribution.

13. A splicing device for splicing optical conductors, said device including at least two electrodes, holding devices for two optical conductors, a current source for striking an arc discharge between the electrodes, said current source having a set point generator for the purpose of setting a preset discharge current, the improvements comprising a sensor for detecting a spatially resolved actual intensity distribution along the direction of the axes of the two optical conductors occurring during splicing, a storage device for storing a spatially resolved reference intensity distribution along the direction of the axes of the two optical conductors, a comparator for comparing the actual intensity distribution with the reference intensity distribution and a controller for correcting the discharge current.

14. A splicing device according to claim 13, wherein the sensor also detects the position of the optical conductors in the holding devices.

* * * * *